US011679266B2

(12) United States Patent
English et al.

(10) Patent No.: US 11,679,266 B2
(45) Date of Patent: Jun. 20, 2023

(54) IMPLANTABLE MEDICAL DEVICE HAVING A BIOCOMPATIBLE CIRCUIT BOARD WITH EMBEDDED ELECTRODES

(71) Applicant: Cardiac Pacemakers, Inc., St. Paul, MN (US)

(72) Inventors: James Michael English, Cahir (IE); Jean M. Bobgan, Maple Grove, MN (US); Keith R. Maile, New Brighton, MN (US); Ron A. Balczewski, Bloomington, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 197 days.

(21) Appl. No.: 17/174,940

(22) Filed: Feb. 12, 2021

(65) Prior Publication Data

US 2021/0252293 A1 Aug. 19, 2021

Related U.S. Application Data

(60) Provisional application No. 62/976,075, filed on Feb. 13, 2020.

(51) Int. Cl.
*A61N 1/375* (2006.01)
*A61B 5/25* (2021.01)
(Continued)

(52) U.S. Cl.
CPC ............ *A61N 1/3754* (2013.01); *A61B 5/076* (2013.01); *A61B 5/25* (2021.01); *A61B 5/686* (2013.01);
(Continued)

(58) Field of Classification Search
CPC .... A61N 1/3754; A61N 1/05; A61N 1/37229; A61B 5/076; A61B 5/25; A61B 5/686;
(Continued)

(56) References Cited

U.S. PATENT DOCUMENTS 6,491,639 B1 * 12/2002 Turcott .................... A61B 5/02
600/504
2006/0276842 A1 * 12/2006 He ...................... A61N 1/37205
607/2

(Continued)

OTHER PUBLICATIONS

Kreuz, J.A. and Edman, J.R. (1998), Polyimide Films. Adv. Mater., 10: 1229-1232. https://doi.org/10.1002/(SICI)1521-4095(199810)10:15<1229::AID-ADMA1229>3.0.CO;2-B (Year: 1998).*

*Primary Examiner* — Eric F Winakur
*Assistant Examiner* — Elina Sohyun Ahn
(74) *Attorney, Agent, or Firm* — Faegre Drinker Biddle & Reath LLP

(57) ABSTRACT

Embodiments of the present disclosure relate to implantable medical devices (IMDs). In an exemplary embodiment, an IMD comprises: a housing including a plurality of feedthroughs extending through the housing, a first electrode, a second electrode, and a biocompatible circuit board disposed around an outer surface of the housing. The biocompatible circuit board comprising a plurality of traces, wherein a first trace of the plurality of traces is coupled to the first electrode and a first feedthrough of the plurality of feedthroughs, and a second trace of the plurality of traces is coupled to the first electrode and a second feedthrough of the plurality of feedthroughs.

17 Claims, 5 Drawing Sheets

(51) Int. Cl.
*A61B 5/07* (2006.01)
*A61B 5/00* (2006.01)
*A61N 1/05* (2006.01)
*A61N 1/372* (2006.01)
*A61L 31/02* (2006.01)

(52) U.S. Cl.
CPC ........... *A61N 1/05* (2013.01); *A61N 1/37229* (2013.01); *A61B 2562/125* (2013.01); *A61B 2562/164* (2013.01); *A61B 2562/166* (2013.01); *A61L 31/028* (2013.01)

(58) Field of Classification Search
CPC ........ A61B 2562/125; A61B 2562/164; A61B 2562/166; A61L 31/028
See application file for complete search history.

(56) References Cited

U.S. PATENT DOCUMENTS

2018/0028824 A1* 2/2018 Pivonka .............. A61N 1/37229
2020/0001094 A1* 1/2020 Iyer ....................... A61N 1/3787

* cited by examiner

IMPLANTABLE MEDICAL DEVICE HAVING A BIOCOMPATIBLE CIRCUIT BOARD WITH EMBEDDED ELECTRODES

CROSS REFERENCE TO RELATED APPLICATION

This application claims priority to Provisional Application No. 62/976,075, filed Feb. 13, 2020, which is herein incorporated by reference in its entirety.

TECHNICAL FIELD

Embodiments of the present disclosure relate to medical devices and systems for sensing physiological parameters and/or delivering therapy. More specifically, embodiments of the present disclosure relate to devices and methods for a biocompatible circuit board of an implantable medical device.

BACKGROUND

Implantable medical devices (IMDs) may be configured to sense physiological parameters and/or provide therapy and may include one or more electrodes for performing aspects of these functions. IMDs may also include antennas for communicating with other devices. Conventionally, devices such as programmers have been used to cause IMDs to take various actions such as for example, marking recordings of physiological parameters, initiating communications with other devices, and the like.

SUMMARY

Exemplary embodiments of the present disclosure include, but are not limited to, the following examples.

In an Example 1, an implantable medical device comprises: a housing including a plurality of feedthroughs extending through the housing; a first electrode; a second electrode; and a biocompatible circuit board disposed around an outer surface of the housing, the biocompatible circuit board comprising a plurality of traces, wherein a first trace of the plurality of traces is coupled to the first electrode and a first feedthrough of the plurality of feedthroughs, and a second trace of the plurality of traces is coupled to the first electrode and a second feedthrough of the plurality of feedthroughs.

In an Example 2, the implantable medical device of Example 1, wherein the first electrode and the second electrode are integrated into the biocompatible circuit.

In an Example 3, the implantable medical device of Example 1 or 2, wherein the biocompatible circuit board comprises a plurality of layers and the plurality of traces are arranged between two layers of the plurality of layers.

In an Example 4, the implantable medical device of any one of Examples 1-3, wherein the biocompatible circuit board is a flexible circuit board.

In an Example 5, the implantable medical device of any one of Examples 1-4, wherein the housing is formed from a conductive material.

In an Example 6, the implantable medical device of any one of Examples 1-5, wherein the biocompatible circuit board further comprises an antenna, and wherein a third trace of the plurality of traces is coupled to the antenna and a third feedthrough of the plurality of feedthroughs.

In an Example 7, the implantable medical device of Example 6, the housing further comprising a non-conductive window, wherein the antenna is positioned proximate to the non-conductive window.

In an Example 8, the implantable medical device of Example 7, wherein the non-conductive window is formed from sapphire.

In an Example 9, the implantable medical device of any one of Examples 6-8, further comprising an isolating layer arranged between the antenna and the housing.

In an Example 10, the implantable medical device of any one of Examples 1-9, further comprising a third electrode and a fourth electrode.

In an Example 11, the implantable medical device of any one of Examples 1-10, further comprising a power supply arranged along substantially an entire length of the housing.

In an Example 12, a method for constructing an implantable medical device, the method comprising: arranging an antenna, a first electrode, and a second electrode on a circuit board substrate; disposing a plurality of traces on the circuit board substrate, wherein a first trace of the plurality of traces couples to the first electrode, wherein a second trace of the plurality of traces coupled to the second electrode, and a third trace of the plurality of traces coupled to the antenna; coupling the first trace to a first feedthrough of the implantable medical device housing; coupling the second trace to a second feedthrough of the implantable medical device housing; coupling the third trace to a third feedthrough of the implantable medical device housing; and arranging the circuit board substrate around the implantable medical device housing.

In an Example 13, the method of Example 12, wherein arranging the circuit board substrate around the implantable medical device housing comprises aligning the antenna with a non-conductive window of the implantable medical device housing.

In an Example 14, the method of Examples 12 or 13, further comprising arranging an isolating layer between the antenna and the implantable medical device housing.

In an Example 15, the method of any one of Examples 12-14, further comprising adhering the circuit board substrate to the implantable medical device housing with epoxy.

In an Example 16, an implantable medical device comprising: a housing including a plurality of feedthroughs extending through the housing; a first electrode; a second electrode; and a biocompatible circuit board disposed around an outer surface of the housing, the biocompatible circuit board comprising a plurality of traces, wherein a first trace of the plurality of traces is coupled to the first electrode and a first feedthrough of the plurality of feedthroughs, and a second trace of the plurality of traces is coupled to the first electrode and a second feedthrough of the plurality of feedthroughs.

In an Example 17, the implantable medical device of Example 16, wherein the first electrode and the second electrode are integrated into the biocompatible circuit.

In an Example 18, the implantable medical device of Examples 16 or 17, wherein the biocompatible circuit board comprises a plurality of layers and the plurality of traces are arranged between two layers of the plurality of layers.

In an Example 19, the implantable medical device of any one of Examples 16-18, wherein the biocompatible circuit board is a flexible circuit board.

In an Example 20, the implantable medical device of any one of Examples 16-19, wherein the housing is formed from a conductive material.

In an Example 21, the implantable medical device of any one of Examples 16-20, wherein the biocompatible circuit board further comprises an antenna, and wherein a third trace of the plurality of traces is coupled to the antenna and a third feedthrough of the plurality of feedthroughs.

In an Example 22, the implantable medical device of Example 21, the housing further comprising a non-conductive window, wherein the antenna is positioned proximate to the non-conductive window.

In an Example 23, the implantable medical device of Example 22, wherein the non-conductive window is formed from sapphire.

In an Example 24, the implantable medical device of any one of Examples 21-23, further comprising an isolating layer arranged between the antenna and the housing.

In an Example 25, the implantable medical device of any one of Examples 16-24, further comprising a third electrode and a fourth electrode.

In an Example 26, the implantable medical device of any one of Examples 16-25, further comprising a power supply arranged along substantially an entire length of the housing.

In an Example 27, an apparatus for supporting components configured to be coupled to an implantable medical device, the apparatus comprising: a first electrode; a second electrode; and a biocompatible circuit board configured to be arranged around a housing of the implantable medical device, the biocompatible circuit board comprising a plurality of traces, wherein a first trace of the plurality of traces is coupled to the first electrode and is configured to be electrically coupled to a first feedthrough of the implantable medical device, and a second trace of the plurality of traces is coupled to the first electrode and is configured to be electrically coupled to a second feedthrough of the implantable medical device.

In an Example 28, the apparatus of Example 27, the circuit board further comprising an antenna, wherein a third trace of the plurality of traces electrically is coupled to the antenna and is configured to be coupled to a third feedthrough of the implantable medical device.

In an Example 29, the apparatus of Example 28, wherein the biocompatible circuit board comprises a plurality of layers and the plurality of traces are arranged between two layers of the plurality of layers.

In an Example 30, the apparatus of Example 29, further comprising an isolating layer arranged between the antenna and a layer of the plurality of layers.

In an Example 31, the apparatus of Example 27, wherein the biocompatible circuit board is made of a flexible material.

In an Example 32, a method for constructing an implantable medical device, the method comprising: arranging an antenna, a first electrode, and a second electrode on a circuit board substrate; disposing a plurality of traces on the circuit board substrate, wherein a first trace of the plurality of traces couples to the first electrode, wherein a second trace of the plurality of traces coupled to the second electrode, and a third trace of the plurality of traces coupled to the antenna; coupling the first trace to a first feedthrough of an implantable medical device housing; coupling the second trace to a second feedthrough of the implantable medical device housing; coupling the third trace to a third feedthrough of the implantable medical device housing; and arranging the circuit board substrate around the implantable medical device housing.

In an Example 33, the method of Example 32, wherein arranging the circuit board substrate around the implantable medical device housing comprises aligning the antenna with a non-conductive window of the implantable medical device housing.

In an Example 34, the method of Example 32, further comprising arranging an isolating layer between the antenna and the implantable medical device housing.

In an Example 35, the method of Example 32, further comprising adhering the circuit board substrate to the implantable medical device housing with epoxy While multiple embodiments are disclosed, still other embodiments of the present disclosure will become apparent to those skilled in the art from the following detailed description, which shows and describes illustrative embodiments of the subject matter disclosed herein. Accordingly, the drawings and detailed description are to be regarded as illustrative in nature and not restrictive.

Figure 1:
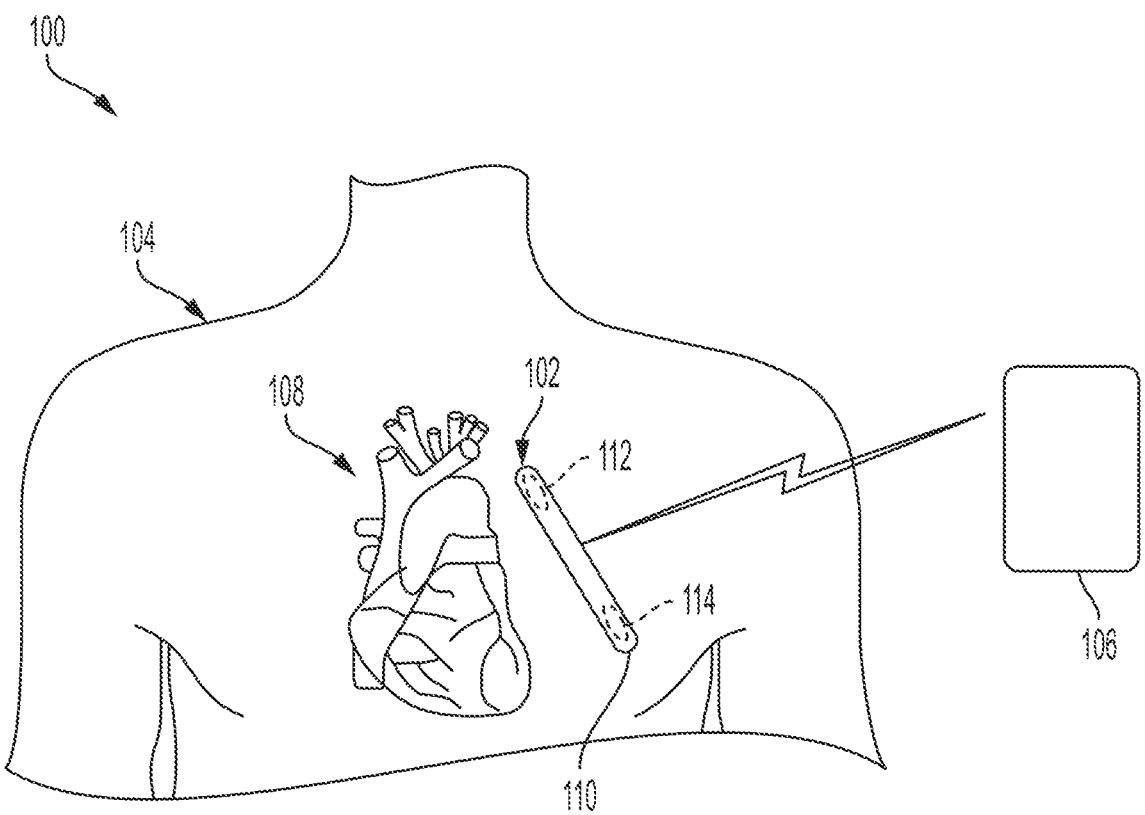
FIG. 1 is a schematic illustration of a system having an implantable medical device (IMD) and a receiving device, in accordance with embodiments of the present disclosure.

While the subject matter disclosed herein is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the subject matter disclosed herein as defined by the appended claims.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

The size of an implantable medical device (IMD) is constrained due to being implanted in a patient. Due to these size constraints, the power supply of the IMD can be a limiting factor in how much functionality can be incorporated into the IMD. As such, transmitting sensor measurements to an external device can be useful for processing the sensor measurements. To transmit the sensor measurements, IMDs often include a header made of a non-conductive material, such as an epoxy. However, including a header further reduces the size of the power supply that can be included in an IMD due to the positioning and size of the headers. The embodiments disclosed herein provide a solution to this problem.

FIG. 1 is a schematic illustration of a system 100 including an IMD 102 implanted within a patient's body 104 and configured to communicate with a receiving device 106. In embodiments, the IMD 102 may be implanted subcutaneously within an implantation location or pocket in the patient's chest or abdomen and may be configured to monitor (e.g., sense and/or record) physiological parameters associated with the patient's heart 108. In embodiments, the IMD 102 may be an implantable cardiac monitor (ICM) (e.g., an implantable diagnostic monitor (IDM), an implantable loop recorder (ILR), etc.) configured to record physiological parameters such as, for example, one or more cardiac activation signals, heart sounds, blood pressure measurements, oxygen saturations, and/or the like.

In embodiments, the IMD 102 may be configured to monitor physiological parameters that may include one or more signals indicative of a patient's physical activity level and/or metabolic level, such as an acceleration signal. In embodiments, the IMD 102 may be configured to monitor physiological parameters associated with one or more other organs, systems, and/or the like. The IMD 102 may be configured to sense and/or record at regular intervals, continuously, and/or in response to a detected event. In embodiments, such a detected event may be detected by one or more sensors of the IMD 102, another IMD (not shown), an external device (e.g., the receiving device 106), and/or the like.

In addition, the IMD 102 may be configured to detect a variety of physiological signals that may be used in connection with various diagnostic, therapeutic, and/or monitoring implementations. For example, the IMD 102 may include sensors or circuitry for detecting respiratory system signals, cardiac system signals, and/or signals related to patient activity. In embodiments, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position.

For purposes of illustration, and not of limitation, various embodiments of devices that may be used to record physiological parameters in accordance with the present disclosure are described herein in the context of IMDs that may be implanted under the skin in the chest region of a patient.

As shown, the IMD 102 may include a housing 110 (shown in FIG. 2) having two electrodes 112A and 114A coupled thereto. In embodiments, the IMD 102 may include any number of electrodes (and/or other types of sensors such as, e.g., thermometers, barometers, pressure sensors, optical sensors, motion sensors, and/or the like) in any number of various types of configurations, and the housing 110 may include any number of different shapes, sizes, and/or features. In embodiments, the IMD 102 may be configured to sense physiological parameters and record the physiological parameters. For example, the IMD 102 may be configured to activate (e.g., periodically, continuously, upon detection of an event, and/or the like), record a specified amount of data (e.g., physiological parameters) in a memory, and communicate that recorded data to a receiving device 106. In the case of an IDM, for example, the IMD 102 may activate, record cardiac signals for a certain period of time, deactivate, and activate to communicate the recorded signals to the receiving device 106.

In embodiments, the receiving device 106 may be, for example, a programmer, controller, patient monitoring system, and/or the like. Although illustrated in FIG. 1 as an external device, the receiving device 106 may include an implantable device configured to communicate with the IMD 102 that may, for example, be a control device, another monitoring device, a pacemaker, an implantable defibrillator, a cardiac resynchronization therapy (CRT) device, and/or the like, and may be an implantable medical device known in the art or later developed, for providing therapy and/or diagnostic data about the patient and/or the IMD 102. In embodiments, the IMD 102 may be a pacemaker, an implantable cardioverter defibrillator (ICD) device, or a cardiac resynchronization therapy (CRT) device. In embodiments, the IMD 102 may include both defibrillation and pacing/CRT capabilities (e.g., a CRT-D device).

The system 100 may be used to implement coordinated patient measuring and/or monitoring, diagnosis, and/or therapy in accordance with embodiments of the disclosure. The system 100 may include, for example, one or more patient-internal medical devices, such as an IMD 102, and one or more patient-external medical devices, such as receiving device 106. The receiving device 106 may be configured to perform monitoring, and/or diagnosis and/or therapy functions external to the patient (i.e., not invasively implanted within the patient's body). The receiving device 106 may be positioned on the patient, near the patient, or in any location external to the patient.

The IMD 102 and the receiving device 106 may communicate through a wireless link. For example, the IMD 102 and the receiving device 106 may be coupled through a short-range radio link, such as Bluetooth, IEEE 802.11, and/or a proprietary wireless protocol. The communications link may facilitate uni-directional and/or bi-directional communication between the IMD 102 and the receiving device 106. Data and/or control signals may be transmitted between the IMD 102 and the receiving device 106 to coordinate the functions of the IMD 102 and/or the receiving device 106. Patient data may be downloaded from one or more of the IMD 102 and the receiving device 106 periodically or on command. The physician and/or the patient may communicate with the IMD 102 and the receiving device 106, for example, to acquire patient data or to initiate, terminate, or modify recording and/or therapy.

As illustrated, because the IMD 102 does not include a header and an antenna arranged at an end of the IMD 102, the housing 110 (of FIG. 2) of the IMD 102 can include a larger volume for the same size IMD 102. As such, the IMD 102 can include more electronics and/or a power supply. However, because the IMD 102 does not include a header having an antenna, the embodiments disclosed herein include alternative embodiments for equipping the IMD 102 with an antenna for transmission, as explained below.

The illustrative system 100 shown in FIG. 1 is not intended to suggest any limitation as to the scope of use or functionality of embodiments of the subject matter disclosed throughout this disclosure. Neither should the illustrative system 100 be interpreted as having any dependency or requirement related to any single component or combination of components illustrated in FIG. 1. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of this disclosure.

Figure 2:
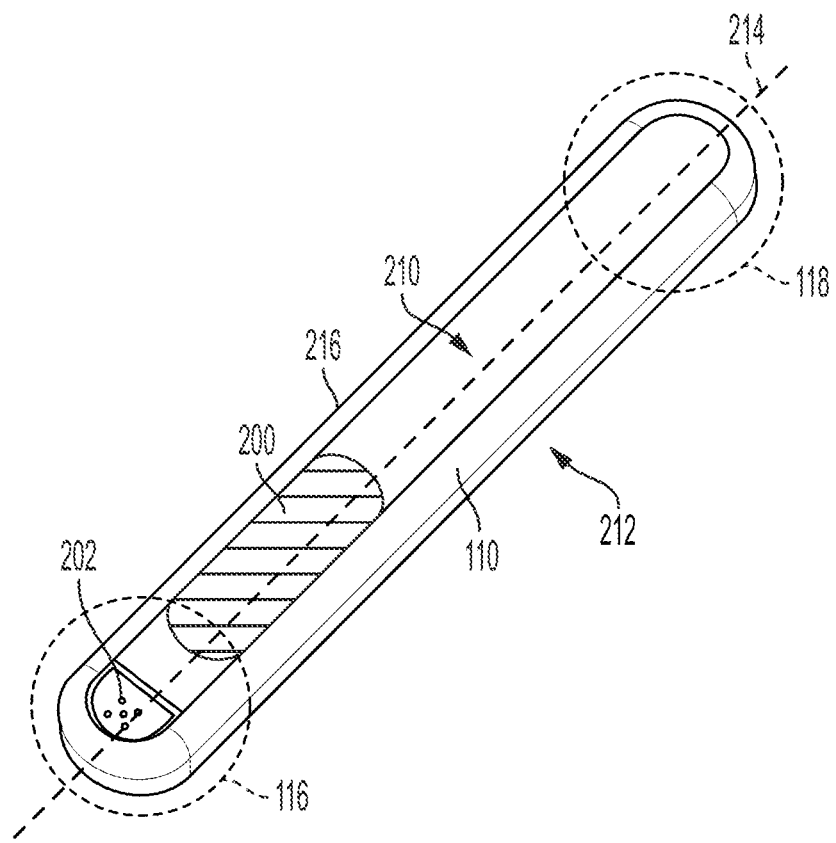
FIG. 2 is a perspective view of a housing of the IMD, in accordance with embodiments of the present disclosure.

FIG. 2 is a perspective view of the housing 110 according to an embodiment as disclosed herein.

According to embodiments, the IMD 102 includes a nonconductive window 200 on an outer surface 216 of the housing 110. In embodiments, the window 200 is located on a frontward facing portion 210 of the outer surface 216. In embodiments, the window 200 may be located on a rearward facing portion 212 of the outer surface 216. In embodiments, the window 200 may be located on both the frontward facing portion 210 and the rearward facing portion 212 (for example, having two windows instead of one) if there are two antennas 206 facing opposing directions from one another. The IMD 102 has a longitudinal axis 214 along which the components (e.g., the components shown in FIG. 4 of the IMD 102 are positioned. The window 200 is made of any suitable nonconductive material such as ceramic, glass, sapphire, etc. In some examples, the window 200 may be transparent or translucent.

At least one feedthrough 202 is disposed at or near one or more ends of the housing 110 along the longitudinal axis 214. In some examples, the housing 110 may include one feedthrough 202, and in some other examples, the housing 110 may include two or more feedthroughs 202. In the example shown in FIGS. 3A and 3B, there are five (5) feedthroughs 202, each of which is electrically coupled with a separate component in the IMD 102 as explained further herein.

The nonconductive window 200 is used to isolate the antenna 206 from the conductive surface of the housing 110. Additionally, or alternatively, the isolation may be performed by inserting an isolating layer (not shown) between the housing 110 and the antenna 206. In some examples, the isolating layer is formed from any nonconductive material such as a suitable polymer using any suitable method such as polymer deposition. The nonconductive window 200 may have advantages over inserting the additional nonconductive isolating layer between the antenna 206 and the housing 110 because the window 200 may reduce the profile (i.e., thickness) of the IMD 102 as compared to when the additional layer is implemented. However, this example is not meant to be limiting and, in embodiments, the window 200 and the non-conductive substrate may be used.

Figure 3A:
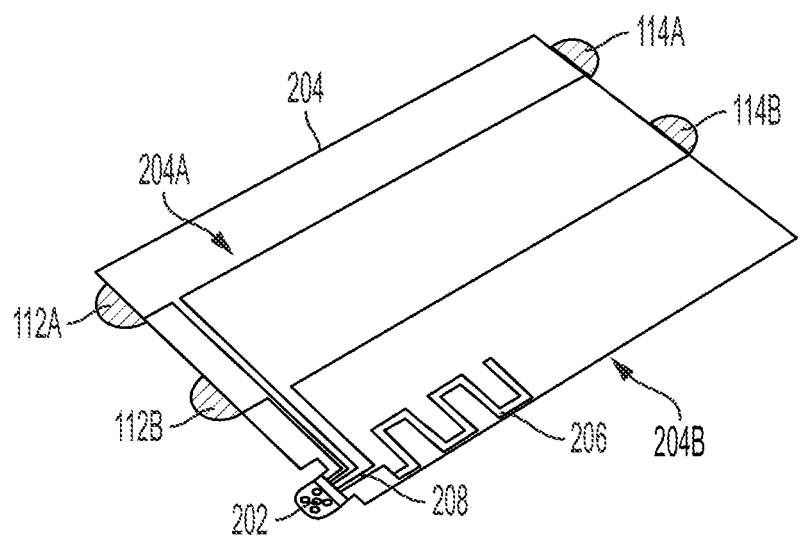
FIG. 3A is a perspective view of a flexible circuit of the IMD shown in FIG. 2, in accordance with embodiments of the present disclosure.
Figure 3B:
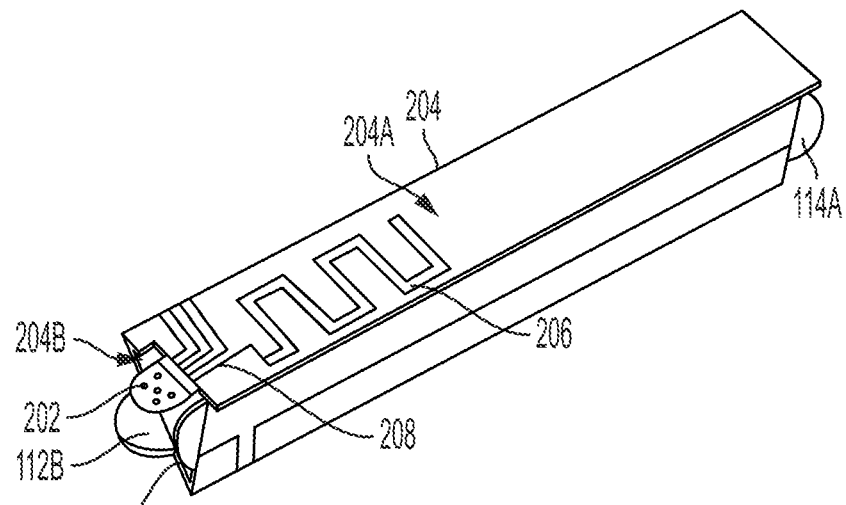
FIG. 3B is a perspective view of the flexible circuit shown in FIG. 3A in a partially bent or folded configuration, in accordance with embodiments of the present disclosure.

FIG. 3A is a perspective view of a circuit board 204 used in the IMD 102 according to an embodiment disclosed herein. The circuit board 204 may be biocompatible. In some examples, the circuit board 204 may be flexible, whereas in some other examples, the circuit board 204 may be rigid. The circuit board 204 may be opaque and made of any suitable material, including but not limited to liquid-crystal polymer (LCP). The circuit board 204 includes two surfaces, a front surface 204A and a back surface 204B. Additionally, or alternatively, the circuit board 204 may include a plurality of layers.

In embodiments, an antenna 206 may be arranged on the front surface 204A, embedded into, and/or arranged between layers of the circuit board 204. In embodiments, the antenna 206 may be arranged proximate to the window 200 to prevent the material of the housing 110 from interfering in the wireless data transmission conducted by the antenna 206. The antenna 206 may be configured for wirelessly communicating data with the receiving device 106.

Additionally, or alternatively, the traces 208 may be arranged on the front surface 204A, embedded into, and/or arranged between layers of the circuit board 204. There may be any number of traces 208 as needed such that the traces 208 electrically couple the feedthroughs 202 with each of the components disposed on the circuit board 204. For example, there are five (5) traces 208, each of which is connected to one of the five (5) feedthroughs 202. And, the five feedthroughs 202 connect to four (4) electrodes and the single antenna (totaling five separate internal components) of the IMD 102. If there are fewer electrodes or more antennas, the number of feedthroughs 202 may change accordingly. In embodiments, the traces 208 are made of any suitable conductive material, such as gold, silver, or platinum alloys, for example. The traces 208 are printed on the circuit board 204 to electrically couple the feedthroughs 202 with each of the first electrode 112A, the second electrode 114A, the third electrode 112B, the fourth electrode 114B, and/or the antenna 206.

In embodiments, a layer of epoxy or any other suitable nonconductive polymer may be applied over the front surface 204A to prevent the traces 208 and/or the antenna 206 from coming into contact with one another and/or the patient's body 104.

In embodiments, the circuit board 204 may be coupled to a first electrode 112A and/or a second electrode 114A. In embodiments, the first and second electrodes 112A, 114A may be incorporated into the circuit board 204. The first and second electrodes 112A, 114A may be arranged on a frontward facing portion 210 of the housing 110.

Additionally, or alternatively, the circuit board 204 may be coupled to a third electrode 112B and/or a fourth electrode 114B. In embodiments, the third and fourth electrodes 112B, 114B may be incorporated into the circuit board 204. The third and fourth electrodes 112B, 114B may be arranged on a rearward facing portion 212 of the housing 110. In embodiments, the electrodes 112, 114 may be used to monitor (e.g., sense and/or record) physiological parameters associated with the patient's body 104.

In embodiments, the circuit board 204 may be wrapped around the housing 110 shown in FIG. 2 by, for example, bending or folding the circuit board 204 around the housing 110. FIG. 2 shows where the electrodes 112A, 114A or electrodes 112B, 114A may overlap the circles 116 and 118 of FIG. 2. As used herein, the term "overlap" may be when the electrodes 112A, 114A at least partially cover one of the circles 116, 118 when observed from an angle that is perpendicular to the longitudinal axis of the IMD.

Figure 4:
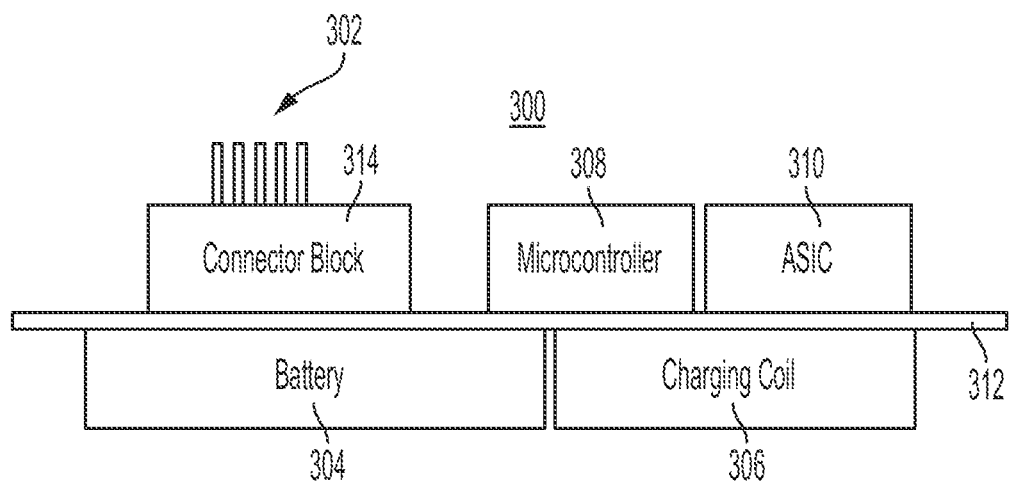
FIG. 4 is a schematic diagram of an electrical subassembly, in accordance with embodiments of the present disclosure.

FIG. 4 shows an electrical subassembly 300 which may be detachably and electrically coupled with the circuit board 204 via the feedthroughs 202. The subassembly 300 is disposed within the housing 110 and includes a battery 304, a charging coil 306 for wireless charging of the battery 304 using an external charging device 318.

The subassembly 300 may also include one or more connector blocks 314 fixed in the housing 110 such that contacts 302 within the connector blocks 314 make electrical contact with the traces 208 of the IMD 102 when the connector blocks 314 are attached to the feedthroughs 202 at the housing 110 of the IMD 102. The number of contacts 302 may be the same as the number of traces 208 such that each of the contacts 302 makes a one-to-one connection with each of the traces 208.

The subassembly 300 may also include control circuitry such as a microcontroller 308, and one or more Application Specific Integrated Circuit (ASICs) 310 as suitable. ASIC(s) 310 may include current generation circuitry for providing stimulation pulses at one or more of the electrodes 112 and 114 and may also include telemetry modulation and demodulation circuitry for enabling bidirectional wireless communications at the antenna 306, battery charging and protection circuitry couplable to charging coil 306, DC-blocking capacitors in each of the current paths proceeding to the electrodes 112 and 114, etc. Components within the housing 110 are integrated via a printed circuit board (PCB) 312.

Figure 5:
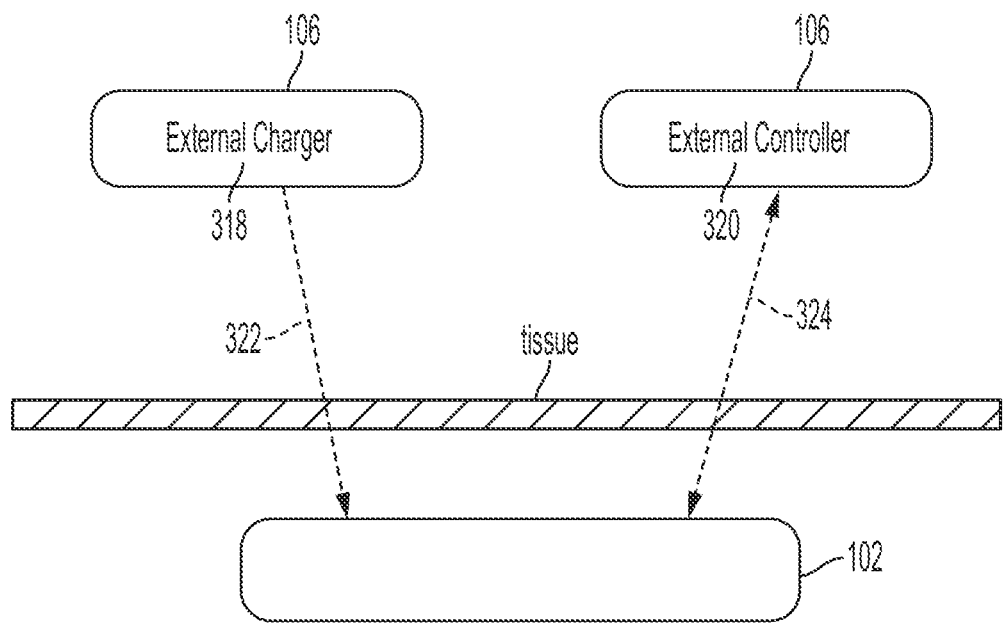
FIG. 5 is a schematic diagram of the IMD and the electrical subassembly in operation with a receiving device, in accordance with embodiments of the present disclosure.

FIG. 5 further shows the external components (for example, the receiving device 106) referenced above, which may be used to communicate with the IMD 102. The receiving device 106 may include an external charger 318 and an external controller 320. The external controller 320 may be used to control and monitor the IMD 102 via a bidirectional wireless communication link 324 passing through a patient's tissue. For example, the external controller 320 may be used to monitor the measurements taken by the electrodes 112 and 114.

Communication on the wireless communication link 324 can occur via magnetic inductive coupling between an antenna (not shown) in the external controller 320 and the antenna 206 in the IMD 102. The magnetic field comprising the link 324 may be modulated via Frequency Shift Keying (FSK) or the like, to encode transmitted data. Other methods including but not limited to short-range RF telemetry (e.g., Bluetooth, WiFi, Zigbee, MICS, etc.) may also be employed.

The external charger 318 can provide power to recharge the battery 304 when the battery 304 is rechargeable. Such power transfer may occur by energizing a charging coil (not shown) in the external charger 318, which produces a magnetic field 322 which then energizes the charging coil 306 in the subassembly 300, which is rectified, filtered, and used to recharge the battery 304.

Furthermore, the antenna 206 as well as the window 200 may be positioned to face the tissue, or positioned to be at the location closest to the skin side or the exterior side of the patient's body, in order to minimize or avoid RF interference by having less body tissue to transmit wireless data therethrough. In addition, the integrated circuitry in some examples includes a Kelvin connection to the first electrode 112 and the second electrode 114. In certain instances, the subassembly 300 may include an accelerometer to determine whether or not the IMD 102 has turned or flipped. The accelerometer may determine periods of electrode inactivity to determine a stable signal and select between the first electrode 112 and the second electrode 114.

Figure 6A:
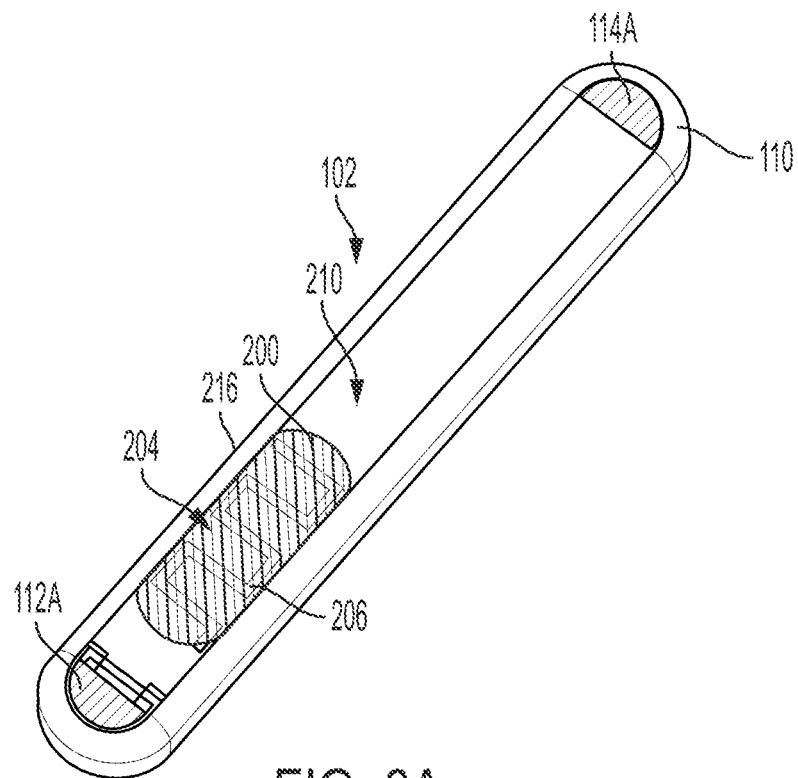
FIG. 6A is a perspective view of the IMD according to an embodiment, in accordance with embodiments of the present disclosure.
Figure 6B:
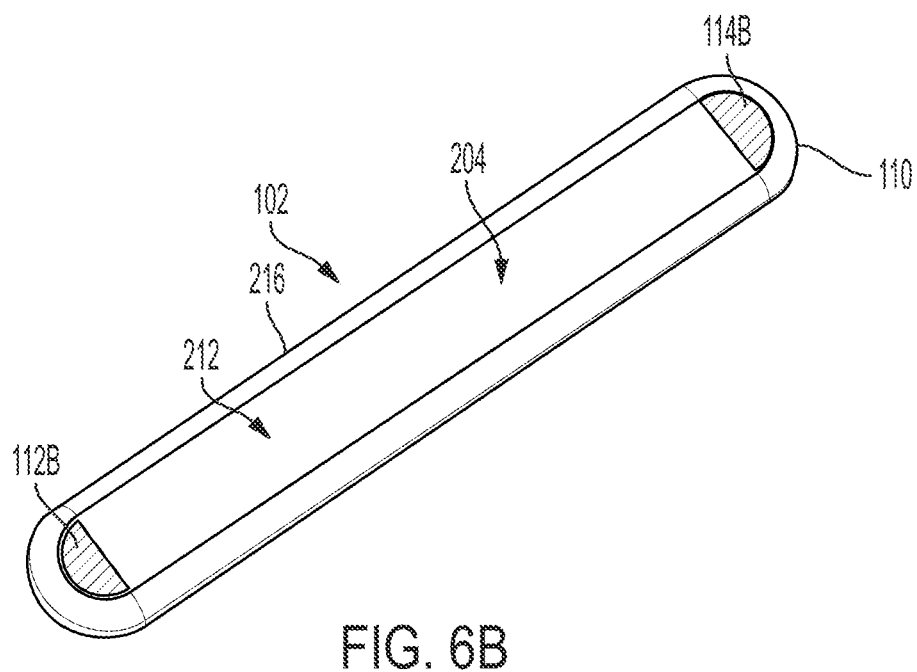
FIG. 6B is another perspective view of the housing of the IMD shown in FIG. 6A.

FIGS. 6A and 6B show perspective views of the IMD 102 from two different angles according to an embodiment as disclosed herein. The housing 110 of the IMD 102 includes the window 200 embedded in the housing 110 such that the window 200 is positioned proximate the antenna 206 and is shown to overlap with the antenna 206. The flexible biocompatible circuit board 204 is wrapped around the outer surface 216 of the housing 110 such that the feedthroughs 202 are in contact with the contacts 302 in the connector blocks 314, and the first electrode 112A overlaps the circle 116 and the second electrode 114A overlaps the circle 118. Further, the third electrode 112B and the fourth electrode 114B are on the rearward facing portion 212.

In some examples, the housing 110 may be formed by having two separate housing portions (for example, one defining the frontward facing portion 210 and the other defining the rearward facing portion 212) combined or conjoined together into one component. In some examples, the combined portions may be laser-welded or ultrasonically welded together onto the housing 110. In some examples, the combined portions may be brazed together using any suitable metal such as gold alloys to form the housing 110. In some examples, the combined portions may be attached together using a suitable adhesive to form the housing 110.

In some examples, the combined portions, along with the circuit board 204, may be shrink-wrapped to form the IMD 102 using any suitable polymer, including but not limited to PVC, polyolefin, polyethylene, and polypropylene. In some examples, an epoxy resin may be placed on the housing 110 such that when the circuit board 204 is disposed around the housing 110, the circuit board 204 is immovably fixed around the housing 110. In some examples, the IMD 102 is sealed to ensure hermiticity using any one or more of the methods outlined above.

The functionality of the first electrode 112A the second electrode 114A, the third electrode 112B, and/or the fourth electrode 114B may be controlled by the integrated circuitry (e.g., microcontroller 308 and/or ASICs 310). For example, the integrated circuitry may be configured to select between the electrodes 112, 114. In addition, the integrated circuitry may be configured to measure sensing capability of the electrodes 112, 114.

In certain instances, the integrated circuitry may be configured to select between one or more of the first electrode 112A, the second electrode 114A, the third electrode 112B, and/or the fourth electrode 114B in response to determining which of the one or more electrodes 112, 114 has the greatest of the sensing capability. The integrated circuitry may be configured to measure impedance on a sensed signal of the electrodes 112, 114 to determining the sensing capabilities of the electrodes 112, 114. The integrated circuitry being configured to select between the electrodes 112, 114 may increase sensing capabilities and signal capture by selecting whichever of the electrodes 112, 114 has the strongest signal for sensing.

The illustrative components shown in the figures are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in the figures may be, in embodiments, integrated with various other components depicted therein (and/or components not illustrated), all of which are considered to be within the ambit of the disclosed subject matter.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An implantable medical device comprising:
   a housing including a non-conductive portion and a plurality of feedthroughs extending through the housing, the housing extending along a longitudinal axis of the implantable medical device between a proximal end and a distal end;
   a first electrode positioned near the proximal end;
   a second electrode positioned near the distal end;

a biocompatible circuit board disposed around an outer surface of the housing and extending parallel with the longitudinal axis, the biocompatible circuit board comprising a plurality of traces, wherein a first trace of the plurality of traces is coupled to the first electrode and a first feedthrough of the plurality of feedthroughs, and a second trace of the plurality of traces is coupled to the second electrode and a second feedthrough of the plurality of feedthroughs; and an antenna aligned with the non-conductive portion, wherein a third trace of the plurality of traces is coupled electrically to the antenna.

2. The implantable medical device of claim 1, wherein the first electrode and the second electrode are integrated into the biocompatible circuit board.

3. The implantable medical device of claim 1, wherein the biocompatible circuit board comprises a plurality of layers and the plurality of traces are arranged between two layers of the plurality of layers.

4. The implantable medical device of claim 1, wherein the biocompatible circuit board is a flexible circuit board.

5. The implantable medical device of claim 1, wherein the housing is formed from a conductive material.

6. The implantable medical device of claim 1, wherein the non-conductive portion is formed from a ceramic material.

7. The implantable medical device of 1, further comprising an isolating layer arranged between the antenna and the housing.

8. The implantable medical device of claim 1, further comprising a third electrode and a fourth electrode.

9. The implantable medical device of claim 1, further comprising a power supply arranged along substantially an entire length of the housing.

10. The implantable medical device of claim 1, wherein the antenna is embedded in the biocompatible circuit board.

11. An apparatus for supporting components configured to be coupled to an implantable medical device, the apparatus comprising:

a first electrode;
a second electrode;
a biocompatible circuit board configured to be arranged around a housing of the implantable medical device, the biocompatible circuit board comprising a plurality of traces, wherein a first trace of the plurality of traces is coupled to the first electrode and is configured to be electrically coupled to a first feedthrough of the implantable medical device, and a second trace of the plurality of traces is coupled to the second electrode and is configured to be electrically coupled to a second feedthrough of the implantable medical device; and an antenna embedded within the biocompatible circuit board and located to be aligned with a non-conductive portion of the housing when the biocompatible circuit board is arranged around the housing, wherein a third trace of the plurality of traces is coupled electrically to the antenna.

12. The apparatus of claim 11, wherein the biocompatible circuit board comprises a plurality of layers and the plurality of traces are arranged between two layers of the plurality of layers.

13. The apparatus of claim 12, further comprising an isolating layer arranged between the antenna and a layer of the plurality of layers.

14. The apparatus of claim 13, wherein the biocompatible circuit board is made of a flexible material.

15. A method for constructing an implantable medical device, the method comprising:

arranging an antenna, a first electrode, and a second electrode on a circuit board substrate;

disposing a plurality of traces on the circuit board substrate, wherein a first trace of the plurality of traces couples to the first electrode, wherein a second trace of the plurality of traces coupled to the second electrode, and a third trace of the plurality of traces coupled to the antenna;

coupling the first trace to a first feedthrough of an implantable medical device housing;

coupling the second trace to a second feedthrough of the implantable medical device housing;

folding the circuit board substrate; and arranging the circuit board substrate around the implantable medical device housing such that the antenna is aligned with a non-conductive window of the implantable medical device housing.

16. The method of claim 15, further comprising arranging an isolating layer between the antenna and the implantable medical device housing.

17. The method of claim 15, further comprising adhering the circuit board substrate to the implantable medical device housing with epoxy.

* * * * *